United States Patent
Doubler et al.

(10) Patent No.: US 7,090,674 B2
(45) Date of Patent: Aug. 15, 2006

(54) BONE FIXATION SYSTEM WITH LOW PROFILE FASTENER

(75) Inventors: Robert L. Doubler, Ida, MI (US); John E. Hammill, Rossford, OH (US)

(73) Assignee: Spinal, LLC, Toleda, OH (US)

( * ) Notice: Subject to any disclaimer, the term of this patent is extended or adjusted under 35 U.S.C. 154(b) by 111 days.

(21) Appl. No.: 10/701,349

(22) Filed: Nov. 3, 2003

(65) Prior Publication Data

US 2005/0096653 A1    May 5, 2005

(51) Int. Cl.
    *A61B 17/56* (2006.01)
(52) U.S. Cl. .......................... 606/61; 606/60
(58) Field of Classification Search ............. 606/60, 606/69, 70, 71, 72, 73, 61
    See application file for complete search history.

(56) References Cited

U.S. PATENT DOCUMENTS

| | | | |
|---|---|---|---|
| 255,428 A | 3/1882 | Graham | |
| 486,196 A | 11/1892 | Ridsdale et al. | |
| 590,294 A | 9/1897 | Archer | |
| 4,378,187 A | 3/1983 | Fullerton | |
| 4,419,026 A | 12/1983 | Leto | |
| 4,836,196 A | 6/1989 | Park et al. | |
| 4,854,304 A | 8/1989 | Zielke | |
| 4,887,595 A | 12/1989 | Heinig et al. | |
| 4,887,596 A | 12/1989 | Sherman | |
| 4,946,458 A | 8/1990 | Harms et al. | |
| 5,002,542 A | 3/1991 | Frigg | |
| 5,110,244 A | 5/1992 | Garman | |
| 5,129,900 A | 7/1992 | Asher et al. | |
| 5,133,717 A | 7/1992 | Chopin | |
| 5,324,150 A | 6/1994 | Fullerton | |
| 5,427,488 A | 6/1995 | Fullerton et al. | |
| 5,443,467 A | 8/1995 | Biedermann et al. | |
| 5,487,744 A | 1/1996 | Howland | |
| 5,549,608 A | 8/1996 | Errico et al. | |
| 5,569,247 A | 10/1996 | Morrison | |
| 5,584,834 A | 12/1996 | Errico et al. | |
| 5,591,166 A | 1/1997 | Bernhardt et al. | |
| 5,613,816 A | 3/1997 | Cabahug | |
| 5,628,740 A | 5/1997 | Mullane | |
| 5,653,765 A | 8/1997 | McTghe et al. | |
| 5,669,911 A * | 9/1997 | Errico et al. .................. | 606/61 |
| 5,683,392 A | 11/1997 | Richelsoph et al. | |
| 5,716,357 A | 2/1998 | Rogozinski | |
| 5,733,285 A * | 3/1998 | Errico et al. .................. | 606/61 |
| 5,749,690 A | 5/1998 | Kutz | |
| 5,788,443 A | 8/1998 | Cabahug | |
| 5,800,108 A | 9/1998 | Cabahug | |
| 5,800,435 A | 9/1998 | Errico et al. | |
| 5,863,293 A * | 1/1999 | Richelsoph .................. | 606/61 |

(Continued)

FOREIGN PATENT DOCUMENTS

EP    0 836 835 A3    7/1998

(Continued)

Primary Examiner—Pedro Philogene
(74) Attorney, Agent, or Firm—McHale & Slavin, PA (57) ABSTRACT

A low profile orthopedic device is used to fix and stabilize bones to correct anomalies in skeletal structure occurring naturally or by trauma. Bone screws are screwed into bones by application of torque. Clamps are movably attached to the screws. Each clamp includes a compression ring. A connecting rod connects several screws through slots in the clamps. The clamps are tightened to hold the rod and the heads in a pre-selected position by linear movement of the compression rings.

6 Claims, 8 Drawing Sheets

U.S. PATENT DOCUMENTS

| | | | |
|---|---|---|---|
| 5,964,760 A | 10/1999 | Richelsoph | |
| 5,997,539 A * | 12/1999 | Errico et al. | 606/61 |
| 6,010,503 A | 1/2000 | Richelsoph et al. | |
| 6,050,997 A | 4/2000 | Mullane | |
| 6,063,090 A | 5/2000 | Schlapfer | |
| 6,090,111 A | 7/2000 | Nichols | |
| 6,102,952 A | 8/2000 | Koshino | |
| 6,132,432 A | 10/2000 | Richelsoph | |
| 6,162,234 A | 12/2000 | Freeland et al. | |
| 6,187,005 B1 * | 2/2001 | Brace et al. | 606/61 |
| RE37,227 E | 6/2001 | Brodbeck | |
| 6,254,602 B1 * | 7/2001 | Justis | 606/61 |
| 6,273,888 B1 * | 8/2001 | Justis | 606/61 |
| 6,355,040 B1 | 3/2002 | Richelsoph et al. | |
| RE37,665 E | 4/2002 | Ralph et al. | |
| 6,416,515 B1 | 7/2002 | Wagner | |
| 6,454,773 B1 * | 9/2002 | Sherman et al. | 606/78 |
| 6,478,798 B1 | 11/2002 | Howland | |
| 6,565,565 B1 | 5/2003 | Yuan et al. | |
| 6,595,992 B1 | 7/2003 | Wagner et al. | |
| 6,602,255 B1 | 8/2003 | Campbell et al. | |
| 6,610,062 B1 | 8/2003 | Bailey et al. | |
| 6,610,063 B1 | 8/2003 | Kumar et al. | |
| 6,623,485 B1 | 9/2003 | Doubler et al. | |
| 6,626,906 B1 | 9/2003 | Young | |
| 2002/0114680 A1 | 8/2002 | Stoewer et al. | |
| 2003/0149487 A1 | 8/2003 | Doubler et al. | |

FOREIGN PATENT DOCUMENTS

EP     0 947 174 A3     5/2001

* cited by examiner

BONE FIXATION SYSTEM WITH LOW PROFILE FASTENER

BACKGROUND OF THE INVENTION

1. Field of the Invention

This invention relates to orthopedic surgery and, in particular, to devices and prosthesis for stabilizing and fixing bones and joints of the body.

2. Description of the Prior Art

Published U.S. Application, US 2003/0149487 A1, published Aug. 7, 2003, teaches the use of a linear movement to apply compressive forces to connect components of an artificial hip joint.

U.S. Pat. No. 6,626,906 issued Sep. 30, 2003 to Young teaches a spinal rod attached to a spinal anchor by a clamp. The clamp is tightened about the anchor by a collet screwed into the clamp. The rod is held in the clamp by a split ring that is reduced in size by the collet. The anchor is placed in the bone by torque and the collet is tightened by additional torque.

U.S. Pat. No. 6,610,063 issued Aug. 26, 2003 to Kumar et al, U.S. Pat. No. 6,610,062 issued Aug. 26, 2003 to Bailey et al, U.S. Pat. No. 6,565,565 issued May 20, 2003 to Yuan et al, U.S. Pat. No. RE 37,665 issued Apr. 16, 2002 to Ralph et al, U.S. Pat. No. 6,478,798 issued Nov. 12, 2002 to Howland and U.S. Pat. No. 5,584,834 issued Dec. 17, 1996 to Errico et al teach a spinal rod coupled to several bone anchors by clamps that require additional torque to be applied to the assembly after the bone screw has been seated in the bone.

In normal practice, the bone screws are each anchored in the bone with a specific amount of torque that approaches the ultimate sustainable force between the screw threads and the bone. The bone screws are then connected together by a rod having sufficient stiffness to maintain the desired skeletal orientation. The connection between the rod and the bone screws must be strong enough to be immobile.

All these prior art spinal fixation devices result in additional torque applied to the assembly, and thereby to the bone screw, to tighten and lock the rod to each of the bone screws. The additional load may strip the purchase between the bone and the threads of the bone screw. To prevent such a result, some tool must be used to counter the torque of locking the rod and the screws. The use of an anti-torqueing tool requires additional coordination by the surgeon or surgeons to prevent slippage.

What is needed in the art is a system for connecting a rod and an embedded bone screw using compressive forces rather than torque.

SUMMARY OF THE PRESENT INVENTION

There are many instances in which it is necessary to stabilize and fix bones and bone fragments in a particular spatial relationship to correct the location of skeletal components due to injury or disease. One group of devices employ a number of bone pins, anchors, or screws placed in bones across a discontinuity in the bone or bone fragments, such as a fracture, or adjacent vertebrae, or a joint, connected by a rod to maintain a predetermined spatial location of the bones. In some cases these devices may be temporary, with subsequent removal, or permanent, in the form of a prosthesis. The devices may be internal or external of the body. The instant device may be used in these applications. However, the preferred embodiment is related to spinal fixation and the description is directed thereto by way of example and not limitation.

DETAILED DESCRIPTION OF THE INVENTION

Figure 1:
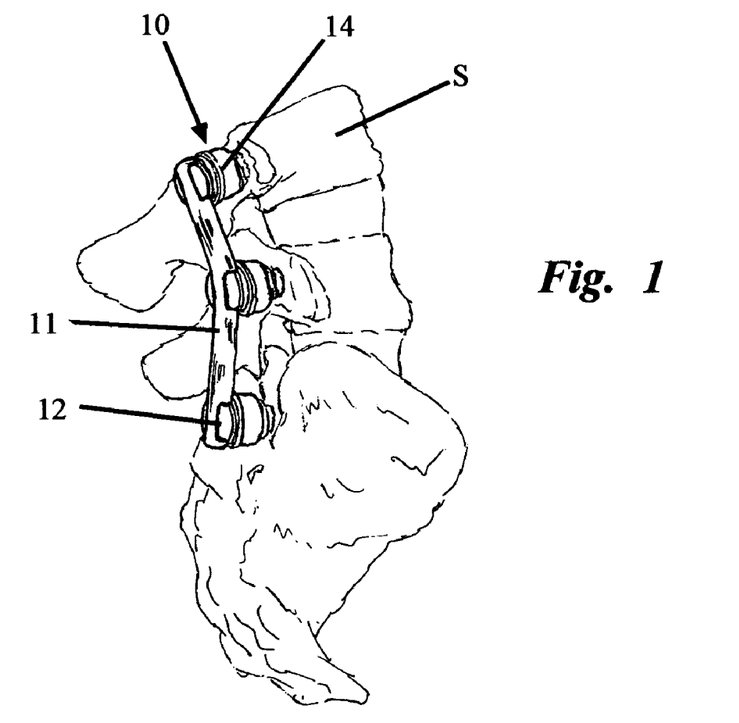
FIG. 1 is a perspective of a portion of the spine with the orthopedic device of this invention in place.
Figure 2:
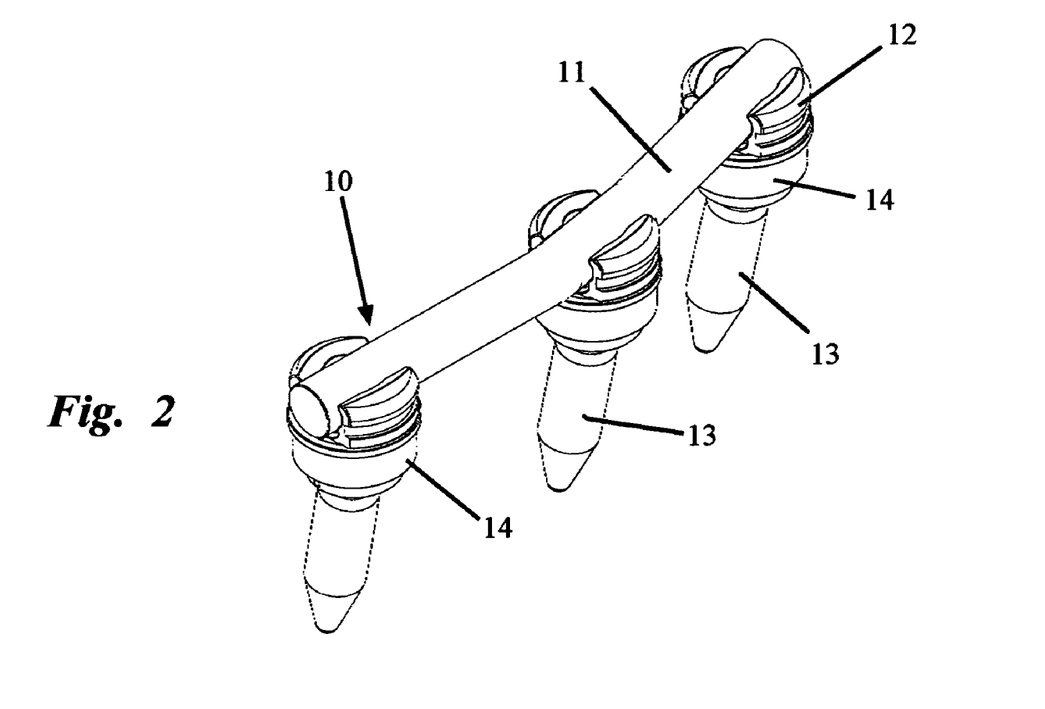
FIG. 2 is a perspective of one embodiment of the orthopedic device of this invention.
Figures 3, 4:
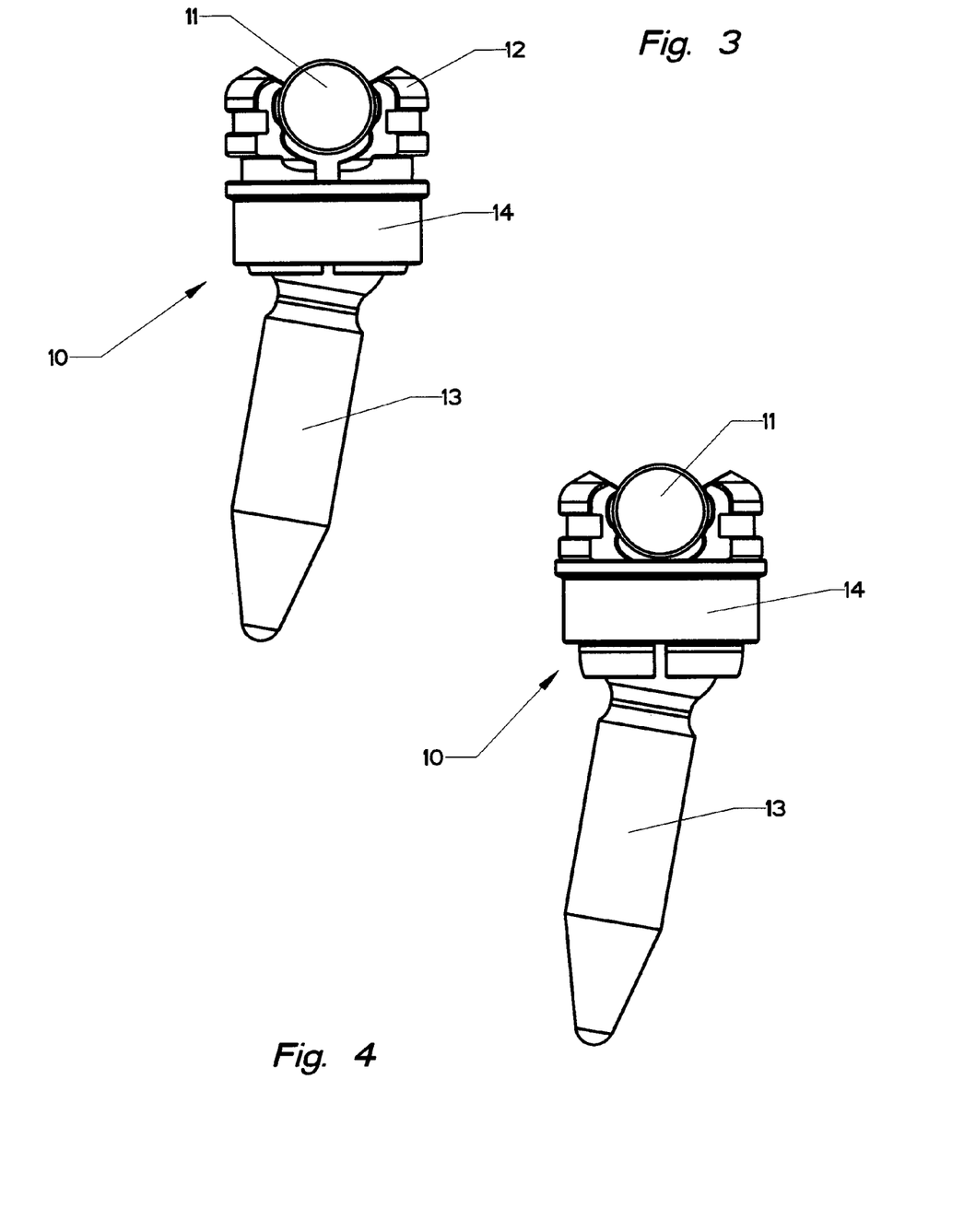
FIG. 3 is an end view, partially in section, of the orthopedic device of this invention with the compression ring in the open position.
FIG. 4 is an end view, partially in section, of the orthopedic device of this invention with the compression ring in the closed position.

FIG. 1 illustrates a portion of the lumbar spine S with a unilateral orthopedic fixation device 10 in place to stabilize and fix the vertebra in relation to each other and the sacrum in order to maintain a more natural curvature. A bilateral installation can be used, if deemed necessary. As shown in more detail in FIG. 2, an elongated connector bar 11 spans the discontinuity between the vertebra and bone screws 13. As shown, the bar has a circular cross section however, other shapes may be used, such as shown for the link 29 in FIG. 13. The bone anchors have an exterior helical thread 60, shown in FIGS. 5–6, by which the bone screws 13 gain purchase in the cancellous bone through application of torque.

Figures 5, 6:
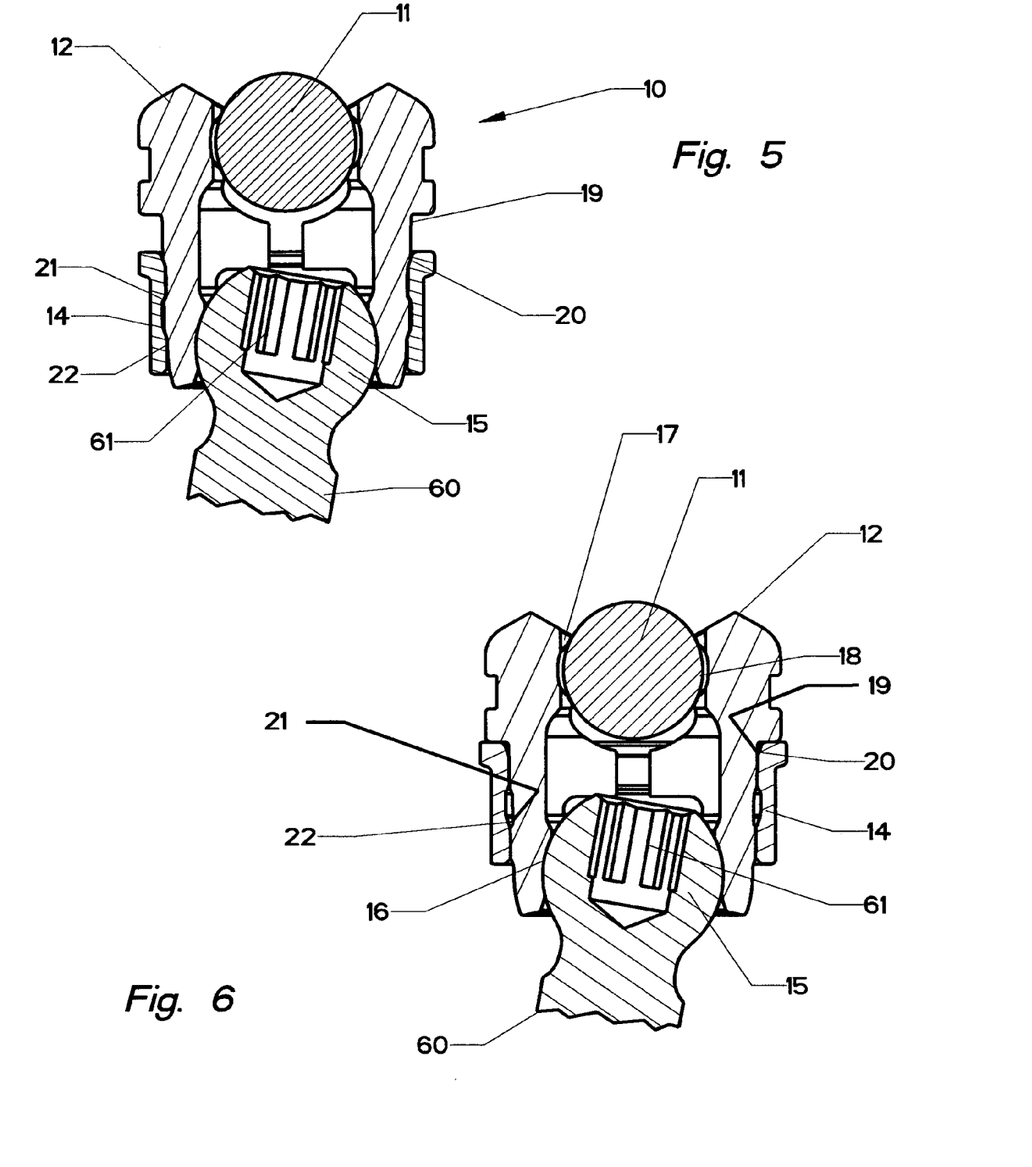
FIG. 5 is a cross section of FIG. 3.
FIG. 6 is a cross section of FIG. 4.
Figure 7:
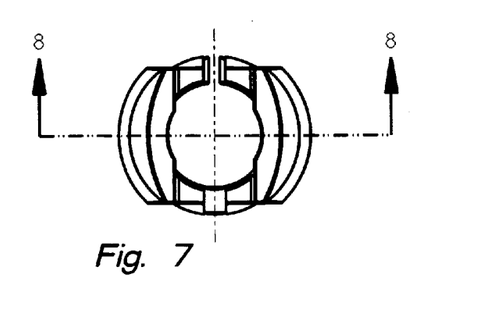
FIG. 7 is a top plan view of the clamp body of this invention.

The torque is applied to the screws by the surgeon using a tool (not shown) that engages the recess 61 in the head 15 of the screw and rotates the screw about its longitudinal axis. The amount of torque is critical to installation and the long life of the prosthesis in that too little does not secure the screw from loosening or backing out and too much causes the stripping of the thread path in the bone and loss of purchase. The surgeon attempts to apply the optimum torque when placing the screws in the bone and additional torque on the bone screw is to be avoided. As shown in FIGS. 5 and 6, the recess 61 is accessible through the clamp body 12 which permits pre-assembly of the screw and clamp, if desired, before placement in the bone.

During the spinal fixation, the several bone screws are threaded into the different vertebrae according to the anatomy of each vertebrae. This results in a series of screws without uniformity in angle or alignment. To compensate for these anomalies, the connection between the head of the screws and the clamp bodies pivots or swivels to capture the connector rod. In some instances, the rod must be bent because the screws are so far out of line or the intended correction is so severe. In other cases, a link may be used to secure the rod relative to the bone screw. To avoid application of any more torque to the bone screw, the connector rod 11 is secured to the bone screw by a linear motion which applies compressive force through clamp 12 to the rod 11 and the head 15 of the screw.

Figure 8:
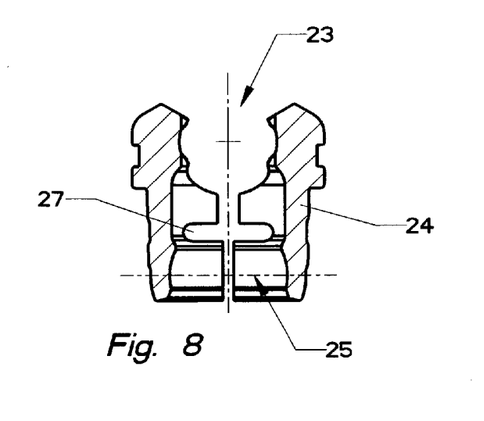
FIG. 8 is a side view, partially in section, of the clamp body of this invention.

The exterior walls 24 of the clamp body 12 are illustrated as generally tubular with a receptacle 25, shown in FIG. 8, at one end and a slot 23 at the other end. The receptacle is of a size to accommodate the head 15 of the bone screw. The slot 23 has upper and lower longitudinal ridges 17 and 18, respectively, to grip the connector rod 11. As shown in FIGS. 5 and 6, the head 15 is spherical and the inside surface 16 of the receptacle is complementary to permit a universal or swivel connection. The orthopedic device has a low profile because the connector rod is recessed in the slot 23 of clamp 12.

Figure 9:
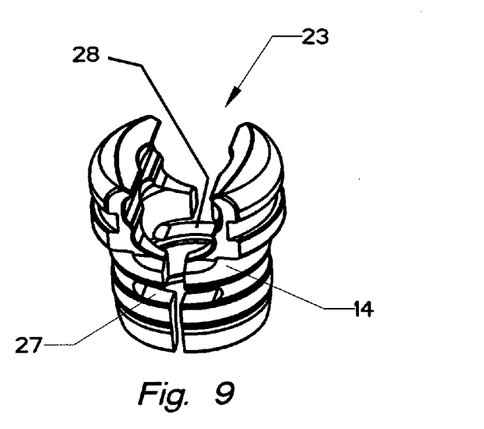
FIG. 9 is a perspective of the clamp body of this invention.
Figure 10:
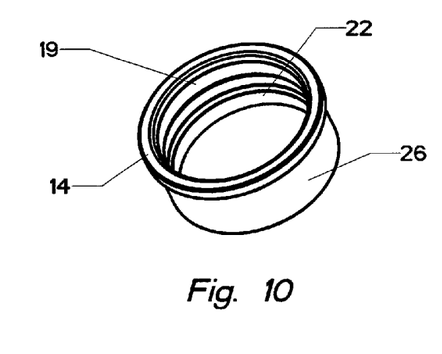
FIG. 10 is a perspective of the compression ring of this invnetion.
Figure 11:
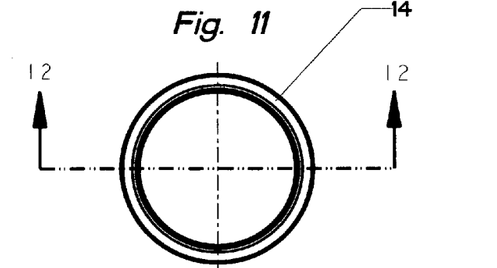
FIG. 11 is a top view of the compression ring of this invention.
Figure 12:
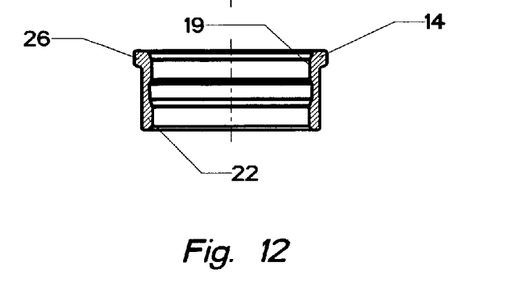
FIG. 12 is a cross section of the compression ring of this invention.
Figures 18, 20:
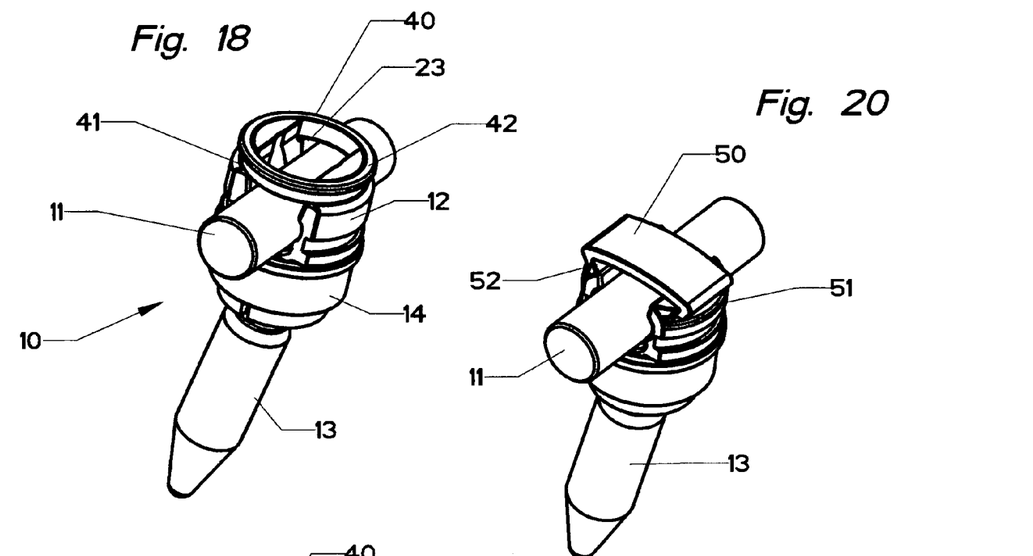
FIG. 18 is a perspective of another embodiment of this invention with the compression ring in the open position.
FIG. 20 is a perspective of another embodiment of this invention with the compression ring in the open position.

The exterior walls 24 of clamp 12 may be tapered or otherwise shaped to provide a change in external diameter along the length. The walls 24 also are relieved with circumferential slots 27 and 28, shown in FIGS. 8–9, to increase the radial flexibility of the clamp. A compression ring 14 is force fit on the exterior walls 24 of the clamp 12 by flexing the tubular walls. The compression ring 14 is movable along the exterior walls from an open position to a closed position. The open position, as shown in FIGS. 5, 18, and 20, allows swiveling movement of the screw head and sliding movement of the connector rod within the clamp 12. In the closed position, shown in FIGS. 6, 19 and 21, the compression ring 14 applies compressive forces between the clamp 12 and the rod 11 and screw 13 that immobilizes the connections. The compression ring 12 has a skirt 26 with spaced inner annular ridges 19 and 22 which engage annular bulges 19 and 21, respectively, on the exterior walls 24 of clamp 12 in the closed position.

The application of the compressive force that immobilizes the components of the orthopedic device is generated by a linear movement of the compression ring relative to the exterior walls of the clamp. This movement to the closed position is accomplished using a simple telescoping instrument (not shown) engaging the clamp and the compression ring so that equal and opposite forces moves the ring without imparting stress to the screw. In the event of remedial surgery, the clamp may be moved to the open position in the same manner.

Figures 13, 14:
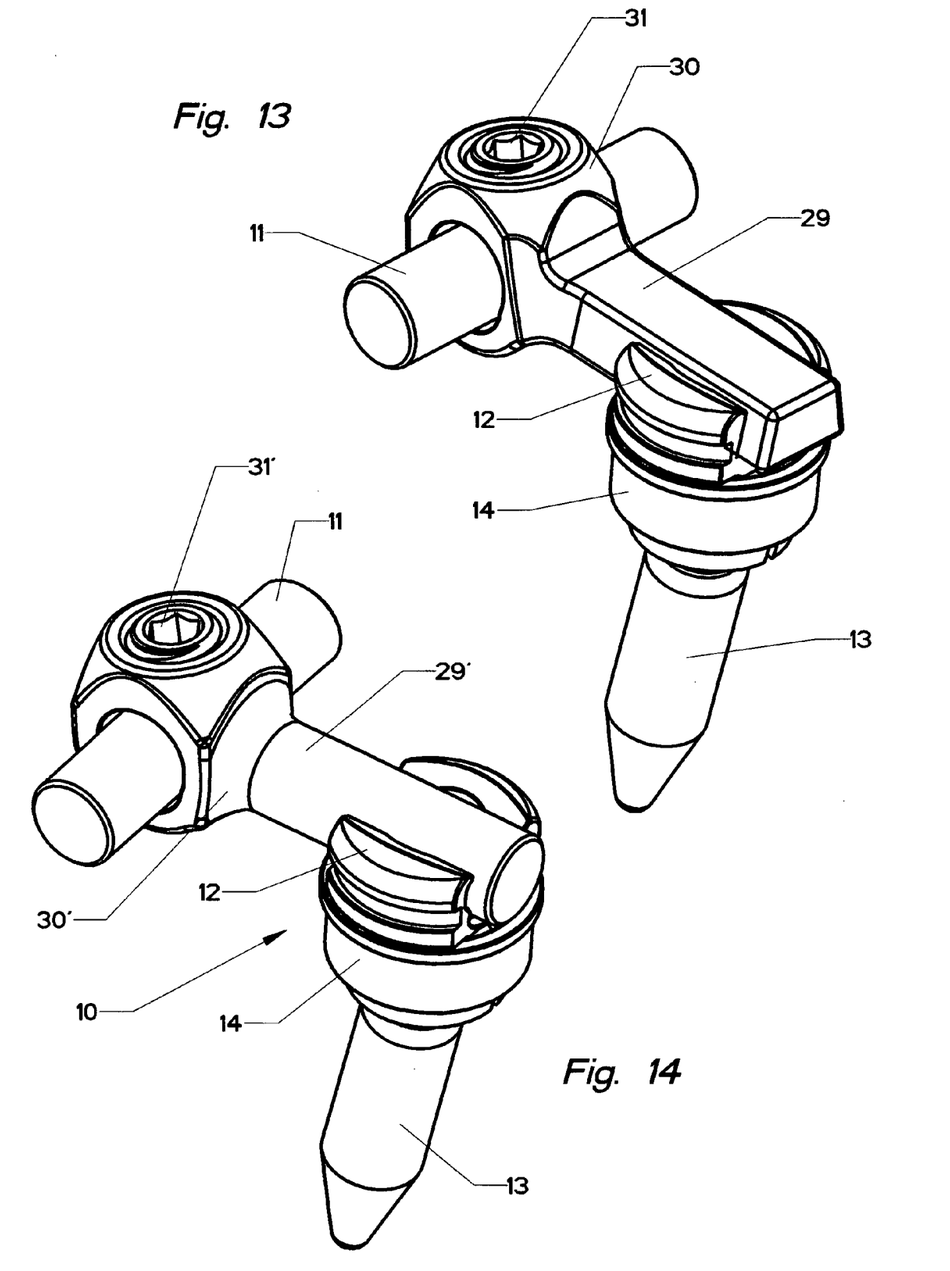
FIG. 13 is a perspective of another embodiment of this invention.
FIG. 14 is a perspective of another embodiment of this invention.

The link 29, shown in FIG. 13, extends the range of the orthopedic device in situations where the connector rod cannot directly contact the slot 23 in the clamp 12. The link may come in different lengths or be customized to the size necessary for a particular patient. The link 29 has an arm similar to the dimensions of a connector rod but of a trapezoidal shape though other shapes may be used. The arm has a journal 30 on one end. The journal 30 is shown as a closed ring however, it may be discontinuous. The journal has a threaded bore with a set screw 31 to secure the link to the connector rod. The other end of the link is secured to the bone screw by the clamp 12 and compression ring 14. In FIG. 14, the link 29' arm is the same or similar in shape to a connector rod. The link has a journal 30' with a set screw 31' to fix the connection with the connector rod 11.

Figure 15:
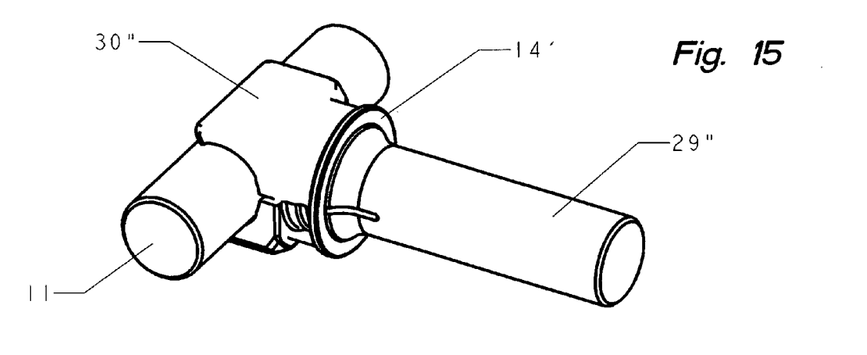
FIG. 15 is a perspective of another embodiment of this invention.
Figure 16:
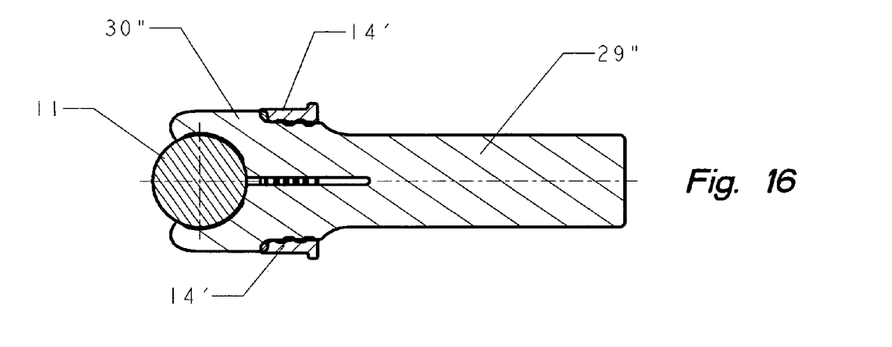
FIG. 16 is a cross section of FIG. 15 showing the compression ring in the open position.
Figure 17:
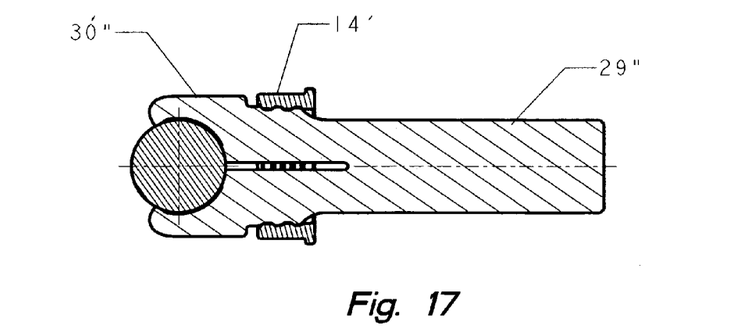
FIG. 17 is a cross section of FIG. 15 showing the compression ring in the closed position.

In FIGS. 15, 16, and 17 another link 29" is illustrated with a journal 30" at one end. The link is similar to a connector rod. The journal 30" is a split sleeve with a compression ring 14' encircling the split sleeve. The compression ring 14' has an open position, shown in FIG. 17, and a closed position, shown in FIG. 16. After adjusting the connection between the link and the connector rod 11, the compression ring is moved to the closed position to secure the link to the connector rod. The other end of the link 29" is secured in the slot of the clamp 12 to complete the tightening of the orthopedic device.

Figure 19:
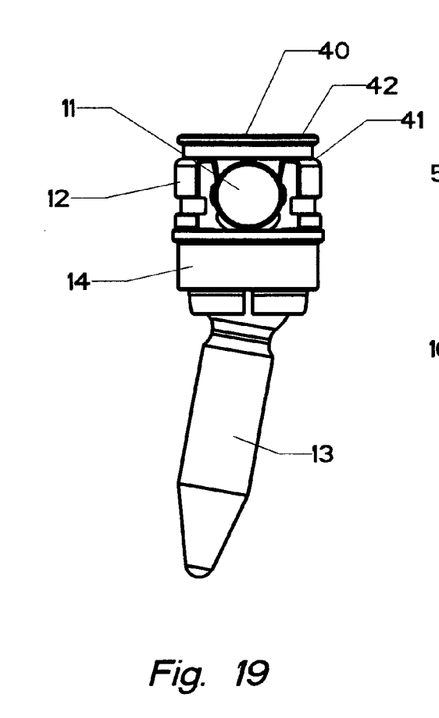
FIG. 19 is a side view of FIG. 18 with the compression ring in the closed position.

FIGS. 18–23 illustrate embodiments of the orthopedic device 10 in which the clamp 12 includes a retainer preventing the inadvertent separation of the connector rod 11 from the clamp. The use of these clamps and retainers is discretionary with the surgeon. In FIGS. 18 and 19, the exterior walls of the clamp 12 extend above the slot 23 as opposing semi-circular projections. An exterior groove 41 is formed in the semi-circular projections resulting in a terminal lip 42. A retainer ring 40 is snapped into and held in place by the groove 41.

Figure 21:
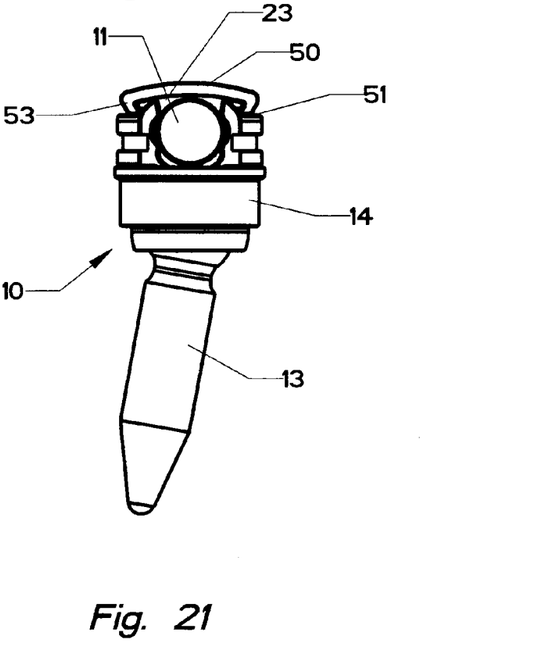
FIG. 21 is a side view of FIG. 20 with the compression ring in the closed position.

FIGS. 20 and 21 illustrate another retainer in the form of a clip 50 which extends across and covers the open slot 23. The ends 53 of the clip are reverse folded to snap over the lip 52 and seat into the groove 51.

Figures 22, 23:
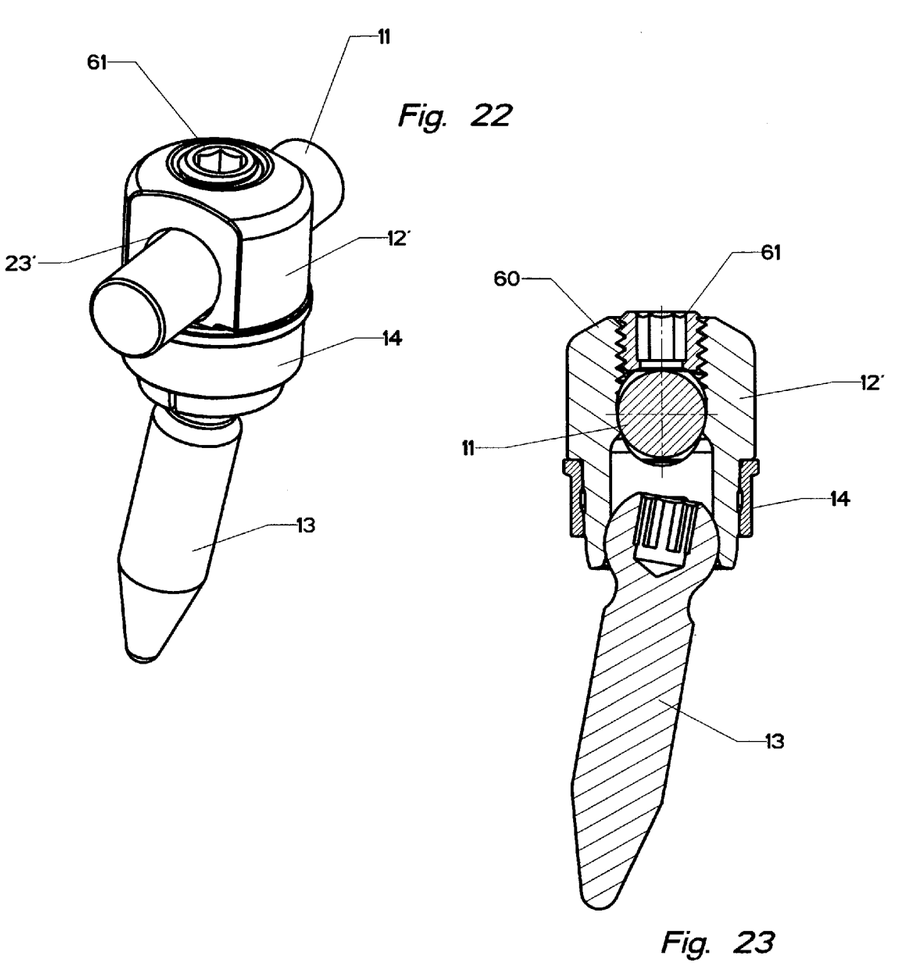
FIG. 22 is a perspective of another embodiment of this invention.
FIG. 23 is a cross section of FIG. 22.

FIGS. 22 and 23 illustrate a clamp 12' with a bore 23' for passage of the connector rod 11. The bore 23' is intersected by a threaded passage 60 with a set screw retainer 61 for holding the connector rod 11 and the clamp 12' together. After the rod 11 is passed through the clamps of an orthopedic device, the compression rings would be moved to the closed position locking the orientation of the rods and screws. The set screws would then be tightened to fix the rod to the clamp. In this way, the torque of tightening the set screw would be absorbed by the rod. The clamp 12' is locked to the screw 13 by compression ring 14, shown in the closed position.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. An orthopedic device for stabilizing bones including at least one bone pin, at least one elongated connector rod and at least one link interconnecting the elongated connector rod and bone pin, each bone pin comprising a shank for penetrating a bone with a head on one end, a clamp universally connected to said head for locking said pin to a link, said clamp having a body including exterior walls forming an inner receptacle enclosing said head, a first compression ring surrounding the outside of said exterior walls in one position, a slot through said exterior walls of said body opposite said receptacle, said slot slidably contacting said link, said first compression ring linearly movable along said outside of said exterior walls to a second position by application of a force consisting of a linear force along a longitudinal axis of said body whereby said exterior walls of said receptacle and said slot exert compressive force securely locking said clamp about said head and said link, said link having an arm with one end and a journal at the other end, said journal has a split sleeve and a second compression ring surrounding the outside of said split sleeve, said second compression ring being movable linearly along said split sleeve by application of a force consisting of a linear force along an axis of said link to move said sleeve from an open position to a closed position, said open position permitting adjustment of said connector rod in said journal and said closed position securing said connector rod and journal together.

2. An orthopedic device of claim 1 wherein said head of said bone pin is approximately spherical and said receptacle has a complementary shape whereby said bone pin and said clamp may be universally oriented.

3. An orthopedic device of claim 1 wherein said shank is formed with an exterior helical thread.

4. An orthopedic device of claim 1 wherein said slot is adjacent said receptacle whereby said head and said link are in close proximity producing a low profile.

5. In an orthopedic system for stabilizing and fixing bones across a discontinuity, at least two bone screws, an elongated connector rod of a length to span the discontinuity, and at least one link, each said bone screw comprising a threaded shank with a head, said head including a means for applying torque to said shank and a means for attaching one end of said link, the other end of said link formed as a clamp, said clamp having an elongated body with exterior walls, a slot extending across said exterior walls of said clamp, said connector rod movably disposed in said slot, a compression ring surrounding said exterior walls in one position linearly along said exterior walls to a second position by application of a force consisting of a linear force along a longitudinal axis of said link whereby said exterior walls exert a compressive force in said slot when said compression ring is moved by said linear force to said second position.

6. In an orthopedic system of claim 5 wherein said connector rod is slidably engaged in said slot when said compression ring is in said one position, said connector rod is held in said slot when said compression ring is in said second position.

* * * * *